(12) United States Patent
Bernhard

(10) Patent No.: US 10,359,365 B2
(45) Date of Patent: Jul. 23, 2019

(54) OPTICAL SENSOR

(71) Applicant: Endress+Hauser Conducta GmbH+Co. KG, Gerlingen (DE)

(72) Inventor: Ralf Bernhard, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 16/032,872

(22) Filed: Jul. 11, 2018

(65) Prior Publication Data
US 2019/0017935 A1 Jan. 17, 2019

(30) Foreign Application Priority Data

Jul. 12, 2017 (DE) .......................... 10 2017 115 661

(51) Int. Cl.
*G01N 21/64* (2006.01)
*G01N 21/01* (2006.01)
(Continued)

(52) U.S. Cl.
CPC ........... *G01N 21/645* (2013.01); *G01N 21/01* (2013.01); *G01N 21/49* (2013.01); *G01N 21/59* (2013.01);
(Continued)

(58) Field of Classification Search
CPC ........... G01N 2021/6463; G01N 21/01; G01N 21/49; G01N 21/59; G01N 21/645; G02B 5/283
See application file for complete search history.

(56) References Cited

U.S. PATENT DOCUMENTS

2001/0035946 A1* 11/2001 Nakase ............... G01C 15/002
356/4.01
2006/0072189 A1* 4/2006 DiMarzio .......... G02B 21/0032
359/368
(Continued)

FOREIGN PATENT DOCUMENTS

AT 513859 B1 8/2014
AU 5897786 A 1/1987
(Continued)

OTHER PUBLICATIONS

Search Report for German Patent Application No. 10 2017 115 661.5, German Patent Office, dated Apr. 10, 2018, 8 pp.

*Primary Examiner* — Mark R Gaworecki
(74) *Attorney, Agent, or Firm* — Christopher R. Powers; PatServe

(57) ABSTRACT

An optical sensor for the ascertainment within a medium of a measured value of a measured parameter of process automation technology, comprising: a light source for transmitting transmission light; a prism; and a receiver for receiving reception light and generating a reception signal therefrom, wherein the measured value is ascertainable from the reception signal, wherein a first optical path from the light source to the medium is defined at least via the prism, wherein a second optical path from the medium to the receiver is defined at least via the prism, wherein the transmission light passes through the prism and is transformed within the medium into reception light, which passes through the prism to the receiver, and wherein the first optical path and the second optical path are essentially parallel to each other.

18 Claims, 2 Drawing Sheets

(51) Int. Cl.
*G01N 21/59* (2006.01)
*G02B 5/28* (2006.01)
*G01N 21/49* (2006.01)
*G01N 33/28* (2006.01)
*G01N 21/51* (2006.01)
*G01N 21/47* (2006.01)

(52) U.S. Cl.
CPC ......... *G01N 33/2847* (2013.01); *G02B 5/283* (2013.01); *G01N 21/51* (2013.01); *G01N 2021/4752* (2013.01); *G01N 2021/6463* (2013.01)

(56) References Cited

U.S. PATENT DOCUMENTS

| | | | | |
|---|---|---|---|---|
| 2007/0138371 A1* | 6/2007 | Marshall | ............... | G01S 7/4812 250/201.3 |
| 2008/0291426 A1* | 11/2008 | Azimi | ............... | G01J 3/02 356/51 |
| 2009/0213361 A1* | 8/2009 | Vander Rhodes | ........ | G01J 3/02 356/51 |
| 2009/0221089 A1* | 9/2009 | Kimura | ............... | B01L 3/5027 436/172 |
| 2009/0237647 A1* | 9/2009 | Azimi | ............... | G01J 3/02 356/51 |
| 2010/0302546 A1* | 12/2010 | Azimi | ............... | G01J 3/02 356/437 |
| 2011/0248904 A1* | 10/2011 | Miyawaki | ........... | G02B 27/017 345/7 |
| 2014/0158911 A1* | 6/2014 | Sahiri | ............... | G01N 21/0303 250/458.1 |
| 2014/0268161 A1* | 9/2014 | Arends | ............. | G01N 21/4738 356/446 |
| 2015/0010878 A1* | 1/2015 | Seibel | ............... | G01N 21/645 433/27 |
| 2015/0260652 A1* | 9/2015 | Verstegen | ................ | G01J 3/44 356/311 |
| 2016/0242647 A1* | 8/2016 | Ishii | .................... | A61B 5/1455 |
| 2016/0266039 A1* | 9/2016 | Suzuki | ................... | G01N 21/59 |
| 2017/0108433 A1* | 4/2017 | Helfmann | ............ | G01J 3/0291 |
| 2017/0179682 A1* | 6/2017 | Ishii | .................... | A61B 5/4887 |
| 2017/0292908 A1* | 10/2017 | Wilk | .................... | G01J 3/0259 |
| 2018/0011015 A1* | 1/2018 | Ishii | .................... | G01N 21/4795 |
| 2018/0084981 A1* | 3/2018 | Wang | ................. | A61B 1/00009 |
| 2018/0184972 A1* | 7/2018 | Carmi | ................... | A61B 5/725 |

FOREIGN PATENT DOCUMENTS

| | | |
|---|---|---|
| AU | 2537995 A1 | 12/1995 |
| AU | 760704 B2 | 12/1999 |
| DE | 69110032 T2 | 12/1995 |
| DE | 19510102 C1 | 10/1996 |
| DE | 19810615 A1 | 9/1999 |
| DE | 69425242 T2 | 12/2000 |
| DE | 69531125 T2 | 4/2004 |
| DE | 10334145 A1 | 2/2005 |
| DE | 102004039564 B4 | 2/2006 |
| DE | 69830598 T2 | 5/2006 |
| DE | 102007020610 A1 | 11/2008 |
| DE | 102007033124 B4 | 1/2009 |
| DE | 102008010435 A1 | 9/2009 |
| DE | 112008003430 T5 | 10/2010 |
| DE | 102011005432 A1 | 9/2012 |
| DE | 102011053003 A1 | 2/2013 |
| DE | 102010060747 B4 | 4/2014 |
| DE | 102012211943 A1 | 6/2014 |
| DE | 102014110341 A1 | 1/2016 |
| DE | 102015101847 B4 | 8/2016 |
| EP | 0620429 A1 | 10/1994 |
| WO | 0022417 A1 | 4/2000 |
| WO | 0025113 A1 | 5/2000 |
| WO | 0140777 A1 | 6/2001 |
| WO | 03078978 A1 | 9/2003 |

\* cited by examiner

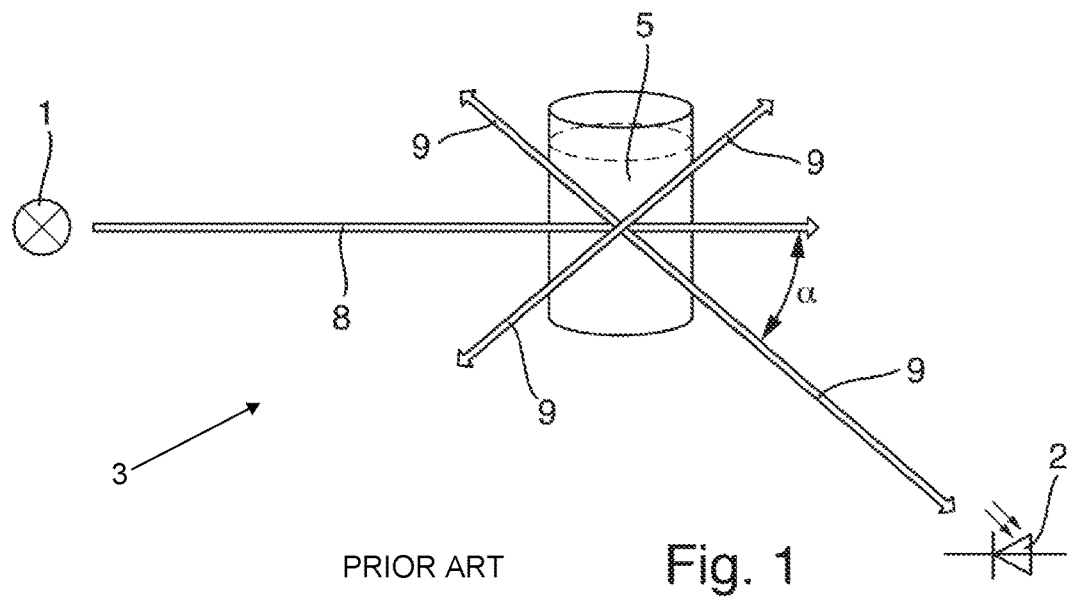
PRIOR ART        Fig. 1
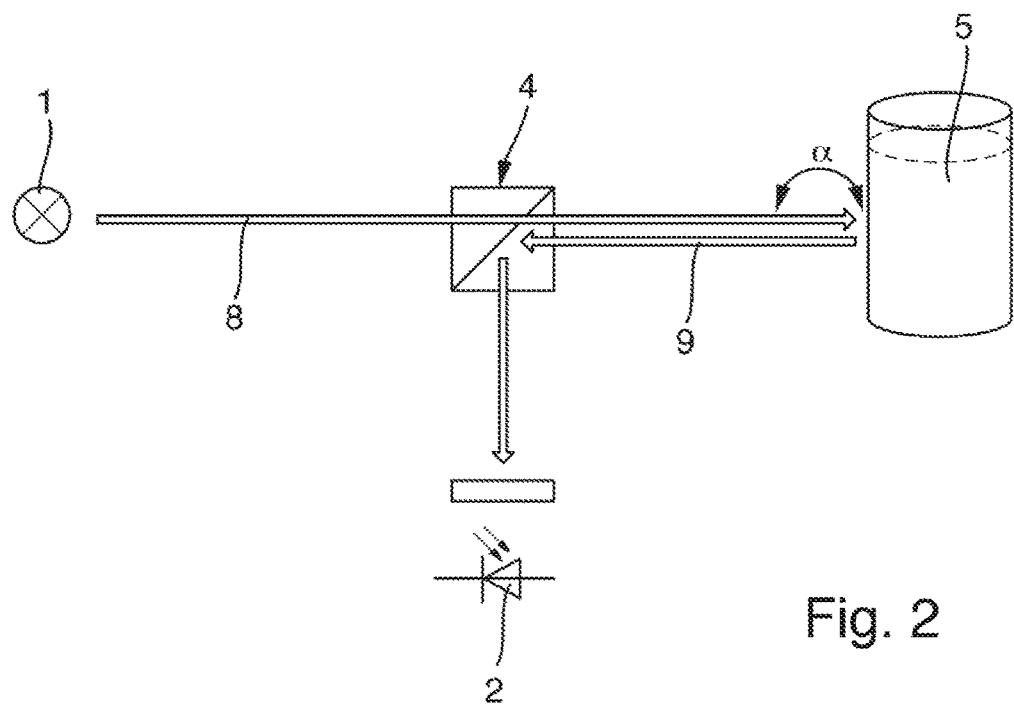
Fig. 2
PRIOR ART

OPTICAL SENSOR

CROSS-REFERENCE TO RELATED APPLICATION

The present application is related to and claims the priority benefit of German Patent Application No. 10 2017 115 661.5, filed on Jul. 12, 2017, the entire contents of which are incorporated herein by reference.

TECHNICAL FIELD

The present disclosure relates to an optical sensor, which is designed for the ascertainment of a measured value of a measured parameter of process automation technology within a medium.

BACKGROUND

The sensor is a fluorescence sensor, for example. The problem upon which the application for patent is based will now be discussed in terms of a fluorescence measurement. In order to measure fluorescence one generally irradiates the medium with a short-wavelength excitation light and detects the longer-wavelength fluorescent light produced by the medium. A fluorescence measurement is typically arranged as depicted in FIG. 1.

For this purpose, the fluorescence sensor 3 comprises a light source 1 and a receiver 2. The light source 1 transmits transmission light, while the receiver 2 receives reception light. Since the fluorescence light radiates in all directions, the light paths of the transmission light and the reception light may, in principle, stand at any angle α with respect to each another. An angle of 0° is not suitable, since, in this instance, the weak fluorescence light is superimposed by the strong excitation light. 90° is quite suitable, provided there is sufficient space to arrange the components. If the measurement array is to be installed in a probe tube, an angle as close as possible to 180° would be chosen, so that light source 1 and receiver 2 are arranged closer together. An angle of 180° is manageable with the help of a beam splitter 4, as can be seen in FIG. 2. For instance, this principle is embodied in the product, "FP360 sc PAK/Öl Fluoreszenz-Sonde [PAK/Oil Fluorescence Probe]," from Hach. However, in this instance, the angle of 180° is present only between the beam splitter 4 and the medium 5. The receiver 2 is again arranged perpendicular to the direction of irradiation and therefore requires lateral installation space, which is often not available.

This problem, however, generally occurs with other optical measurements as well, for instance, with scattered light or absorption measurements.

SUMMARY

To solve this problem, the present disclosure proposes a space-saving optical sensor.

The problem is solved by an optical sensor which is designed to ascertain a measured value of a measured parameter of process automation technology within a medium, comprising: at least one light source for transmitting transmission light; a prism; and at least one receiver for receiving reception light, wherein a reception signal can be produced from the reception light, and wherein the measured value can be ascertained from the reception signal, wherein a first optical path to the medium is produced at least via light source and prism, wherein a second optical path from the medium to the receiver is produced at least via the prism, wherein, in doing so, the transmission light passes through the prism, the transmission light is converted into reception light within the medium, and the reception light passes through the prism, and wherein the first optical path and the second optical path are essentially parallel to each other on the side of the prism facing away from the medium.

In this way, the components for the light source or the receiver can be arranged parallel to each other. The light source and receiver lie close to one another, and the entire assembly may therefore be installed in a small tube diameter.

In one embodiment, the sensor comprises a tube-shaped housing, and the light source, prism, and receiver are arranged within the housing.

In one embodiment, the housing has a diameter of 35-75 mm. External diameters of 40 mm and 68 mm shall be given here as examples.

By means of the above-described arrangement, the components for the light source or receiver can each be arranged parallel to the longitudinal axis of a tube-shaped housing, which then obviates any space problem.

In one embodiment, the housing comprises an optical window which is translucent at least with respect to the transmission light and reception light, wherein the prism and the window are either separated, cemented, bonded, merged, or formed from a single piece. This results in simplification of manufacturing, and the housing can thereby be arranged close to the medium to be measured.

In one embodiment, the light source is designed as a light-emitting diode and/or the receiver as a photodiode.

In one embodiment, the transmission light is converted within the medium into reception light by means of fluorescence.

In one embodiment, the light source emits UV light having a wavelength of 200-400 nm.

In one embodiment, the first optical path comprises a lens and/or a filter.

In one embodiment, the second optical path comprises a lens and/or a filter.

In one embodiment, at least one of the lenses has a focal length of 2-20 mm.

In one embodiment, the filter or filters are designed as wavelength filters, with the filter or filters being, in particular, designed as interference filters. The optical path is thus designed in such a way that the transmission light or the reception light essentially passes through the filter or filters perpendicularly.

In one embodiment, the distance between light source and window is 2-6 cm.

In one embodiment, the sensor is designed to ascertain the oil-in-water content.

In one embodiment, the prism is designed as a straight prism having a triangular base. The triangle is an isosceles triangle, wherein its base points in the direction of the medium. In one embodiment, the prism is a right angle prism. This is a relatively inexpensive component.

In one embodiment, the external diameter of the housing is selected from a range of 8-15 mm—for example, 12 mm. The above-described embodiments are equally applicable in this instance.

In one embodiment, the light source and/or the receiver are arranged outside of the housing.

In one embodiment, the reception light or the transmission light are conducted to the prism or away from the prism by means of one or more optical fibers.

After passing through the prism, the transmission light is absorbed within the medium and scattered. After again passing through the prism, the scattered light is conducted toward the receiver, as described above.

In one embodiment, the light source is provided as a broadband light source.

In one embodiment, the receiver is a spectrometer.

BRIEF DESCRIPTION OF THE DRAWINGS

This will be explained in more detail with reference to the following figures. Shown are:

FIG. 1 shows a schematic view of a sensor arrangement according to the prior art;

FIG. 2 shows a schematic view of an alternative sensor arrangement according to the prior art;

In the figures, the same features are identified with the same reference symbols.

DETAILED DESCRIPTION

Figure 3:
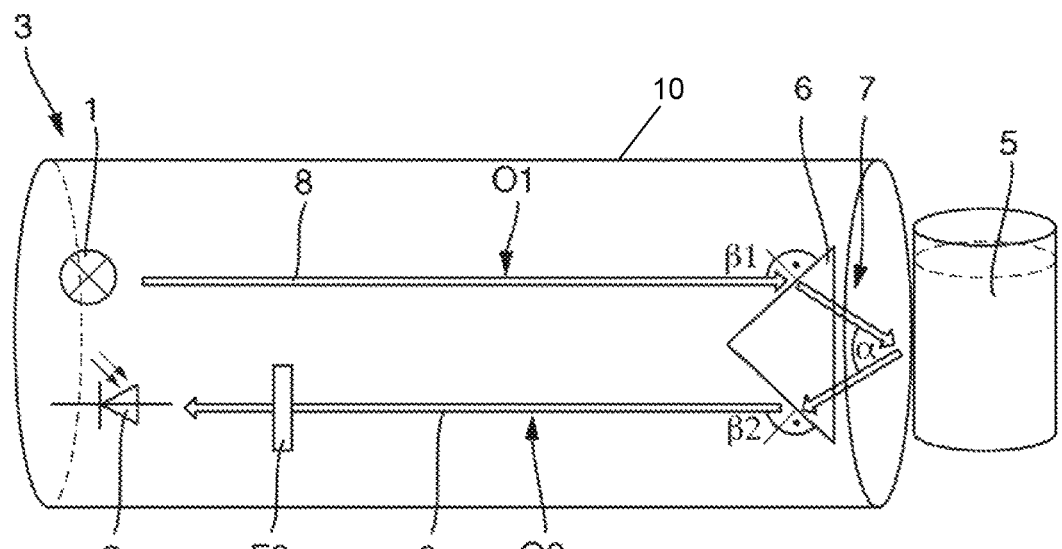
FIG. 3 shows a schematic view of a sensor according to the present disclosure.

The claimed sensor in its entirety bears the reference symbol 3 and is shown schematically in FIG. 3.

In the following, in a first exemplary embodiment, only the differences from the above-described prior art shall be discussed. The sensor 3 is suited to the ascertainment of the oil-in-water content of a medium 5.

A light source 1 transmits transmission light 8 in the direction of the medium 5. The light source is a UV light source, which emits light having a wavelength of 200-400 nm. The transmission light 8 encounters a prism 6 at an angle $\beta 1$. The prism 6 is a right angle prism. The base points toward the medium to be measured. A first optical path O1 from the light source 1 to the prism 6 is produced. The optical path O1 may also contain one or more lenses L1 or filters F1 (see below).

The transmission light 8 is transformed, in part, into reception light 9 by fluorescence within the medium 5. The reception light 9 takes the path in the direction of the receiver 2 via the prism 6. The reception light 9 exits the prism at an angle $\beta 2$. The receiver 2 is a photodiode. A second optical path O2 from the prism 6 to the receiver 2 is produced. The optical path O2 may also contain one or more lenses L2 or filters F2 (see below). The first and second optical paths O1, O2 are essentially parallel to each other on the side of the prism facing away from the medium.

The light source 1, prism 6, and detector 2 are arranged within a housing 10. The housing is tube-shaped, having a diameter of 35-75 mm. The housing 10 comprises an optical window 7, which is translucent at least with respect to transmission light 8 and reception light 9, wherein the prism 6 and the window 7 are either cemented, bonded, merged, or formed from a single piece. The distance from the light source 1 or the receiver 2 to the window 7 is about 2-6 cm.

The filter or filters F1, F2 are formed as wavelength filters, more specifically, as interference filters.

Figure 4:
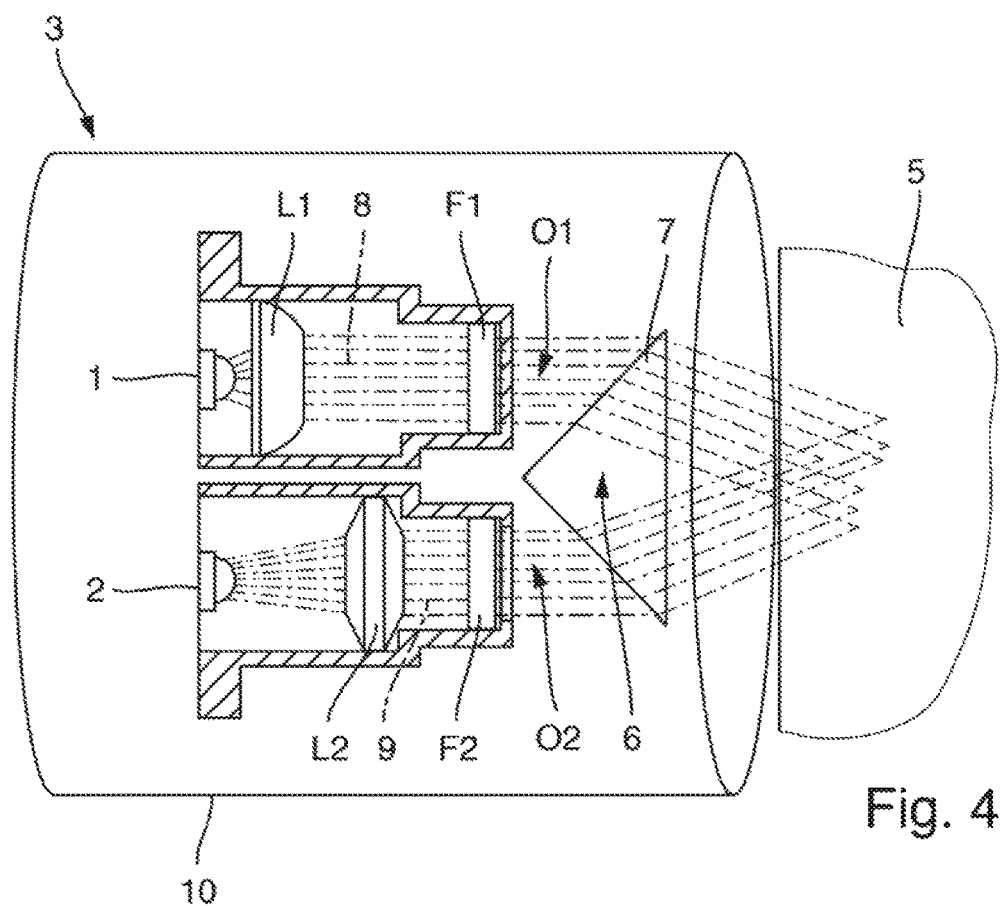
FIG. 4 shows an optical simulation of the sensor according to the present disclosure.

FIG. 4 shows an optical simulation of the sensor 3. Transmission light 8 from the light source 1 is, in the process, first transmitted through a lens L1, and then through a filter F1. After fluorescence within the medium 5, the reception light 9 first passes through the filter F2, and then through the lens L2. Lenses L1, L2 ensure that only essentially parallel light strikes the filters F1 and F2.

The lenses L1, L2 have focal lengths between 2-20 mm. Since the optical paths O1 and O2 run parallel, the lenses L1 and L2 have a maximum diameter of one-half the diameter of the housing 10, for example, 15-40 mm.

In addition, the light source 1 is preferably located approximately at the focal point of the lens L1, and the detector 2 is preferably located approximately at the focal point of the lens L2.

In a second exemplary embodiment, the diameter of the housing 10 is smaller than described above, i.e., in the approximate range of 8-15 mm, for example, 12 mm. The above-described principle involving the first and second optical paths O1 and O2, which run parallel, as well as the prism 6, is likewise applicable in this embodiment. Owing to the smaller diameter, in one embodiment, the light source 1 and the receiver 2, as well as the lenses L1, L2 and the filters F1, F2, are arranged outside of the housing 10. In one embodiment, the lenses L1, L2 and the filters F1, F2 may be dispensed with. The light source 1 is formed as a broadband light source, e.g., in the wavelength range of 400-2,500 nm. The receiver 2 is designed as a spectrometer. In this instance, one or both optical paths O1 and/or O2 may be formed by means of an optical fiber or as uninterrupted beams. The transmission light 8 is transformed into reception light 9 within the medium 5. In the medium 5, part of the transmission light 8 is absorbed, and part of it is scattered. The portion scattered at an angle $\alpha$ is the reception light 9, which is received by the receiver 2 after passing through the prism 6.

The invention claimed is:

1. An optical sensor for determining a measured value within a medium of a measured parameter of process automation technology, comprising:
    a light source adapted to generate transmission light;
    a prism, wherein the transmission light is refracted by and passes through the prism and into the medium, within which reception light is generated by fluorescence or scattering of the transmission light, such that the transmission light and reception light travel independent paths; and
    a receiver adapted to receive the reception light from the medium via the prism and to generate a reception signal from the reception light, wherein the measured value is determined from the reception signal,
    wherein a first optical path is defined from the light source to the prism, and a second optical path is defined from the prism to the receiver, and
    wherein the first optical path and the second optical path are substantially parallel to and independent from each other on a side of the prism opposite the medium.

2. The sensor of claim 1, further comprising a housing including a window that is at least translucent with respect to transmission light and the reception light, wherein the prism and window are separated, cemented, bonded, merged or a single, integral piece.

3. The sensor of claim 2, wherein the housing has a diameter of 35-75 mm.

4. The sensor of claim 2, wherein the housing is generally tube-shaped, and the light source, prism and receiver are disposed within the housing.

5. The sensor of claim 1, wherein the light source is a light-emitting diode and/or the receiver is formed as a photodiode.

6. The sensor of claim 1, wherein the light source emits UV light having a wavelength of 200-400 nm.

7. The sensor of claim 1, wherein the transmission light is transformed by fluorescence into the reception light within the medium.

8. The sensor of claim 1, further comprising a first lens and/or a first filter arranged in the first optical path.

9. The sensor of claim 8, wherein the first lens has a focal length of 2-20 mm.

10. The sensor of claim 8, wherein the first filter is a wavelength filter.

11. The sensor of claim 8, wherein the first filter is an interference filter.

12. The sensor of claim 1, further comprising a second lens and/or a second filter arranged in the second optical path.

13. The sensor of claim 12, wherein the second lens has a focal length of 2-20 mm.

14. The sensor of claim 12, wherein the first filter is a wavelength filter.

15. The sensor of claim 12, wherein the second filter is an interference filter.

16. The sensor of claim 1, wherein the distance between light source and window is 2-6 cm.

17. The sensor of claim 1, wherein the sensor is adapted for the determining the oil-in-water content of the medium.

18. The sensor of claim 1, wherein the transmission light is transformed into the reception light within the medium via absorption and scattering.

* * * * *